United States Patent [19]

Christiansen et al.

[11] Patent Number: 4,980,471

[45] Date of Patent: Dec. 25, 1990

[54] PREPARATION OF PIPERAZINONES FOR USE AS SULFUR DIOXIDE ABSORBENTS

[75] Inventors: Steven H. Christiansen; David A. Wilson, both of Richwood; Dane Chang, Houston, all of Tex.

[73] Assignee: The Dow Chemical Company, Midland, Mich.

[21] Appl. No.: 418,292

[22] Filed: Oct. 6, 1989

[51] Int. Cl.$^5$ ............................................ C07D 241/08
[52] U.S. Cl. .................................................... 544/384
[58] Field of Search ........................................ 544/384

[56] References Cited

U.S. PATENT DOCUMENTS

| | | | |
|---|---|---|---|
| 2,633,467 | 2/1952 | de Benneville | 544/384 |
| 2,649,450 | 8/1953 | Strong et al. | 544/384 |
| 2,700,668 | 1/1955 | Strong et al. | 544/384 |
| 4,170,650 | 10/1979 | Morris et al. | 544/384 |
| 4,530,704 | 7/1985 | Jones et al. | 544/384 |
| 4,767,860 | 8/1988 | Dunmore et al. | 544/384 |
| 4,783,327 | 11/1988 | Treybig et al. | 544/384 |
| 4,814,443 | 3/1989 | Treybig et al. | 544/384 |

Primary Examiner—Glennon H. Hollrah
Assistant Examiner—James H. Turnipseed

[57] ABSTRACT

The 2-piperazinones are made by reacting a 1-cyano-1-hydroxyalkane with ethylenediamine or a substituted ethylenediamine in aqueous solution. The process to make the 2-piperazinones suitable as a regenerable sulfur dioxide absorbing medium requires that the cyano compound be present in at least a molar equivalent amount to the diamine and that the resulting 2-piperazinone product be sparged with an inert gas.

22 Claims, No Drawings

PREPARATION OF PIPERAZINONES FOR USE AS SULFUR DIOXIDE ABSORBENTS

BACKGROUND OF THE INVENTION

Piperazinones are useful compounds which are good absorbents for removing $SO_2$ from gas streams. Piperazinones and substituted piperazinones are known and they can be prepared by several methods. N-alkyl- and N,N'-dialkylpiperazinones have been prepared by reacting an N-substituted alkylenediamine with a 2-oxoaldehyde which is disclosed in U.S. Pat. No. 4,767,860 and N-substituted hydroxyalkylpiperazinones have been prepared by the reaction of the appropriate piperazinone or of certain substituted piperazinones with an alkylene oxide or the analogous chlorohydrin. This reaction is described in U.S. Pat. No. 2,633,467 and in *Chimie Therapeutique,* May–June, 1969, No. 3, pp. 167—173. Recently issued U.S. Pat. No. 4,814,443 discloses a method of making these hydroxyalkyl-substituted compounds by reacting an $\alpha,\beta$-diketone, e.g. glyoxal, or an alkyl-substituted derivative of glyoxal, with an N-hydroxyalkylalkylenediamine.

An early process, described in U.S. Pat. No. 2,649,450, reacts an N,N'-dialkylethylenediamine with a carbonyl compound and HCN to obtain a 1,4-dialkyl-2-piperazinone. In an alternate process described in the same patent the amine was reacted with a ketone cyanohydrin. In U. S. Pat. No. 2,700,668, a process for making 2-piperazinone is described wherein ethylenediamine and glycolonitrile are reacted together.

SUMMARY OF THE INVENTION

A process for making piperazinones which are useful as sulfur dioxide absorbing compounds, including 2-piperazinone and substituted derivatives thereof. The process reacts a 1-cyano-1-hydroxyalkane with ethylenediamine or its substituted derivatives in aqueous solution. The cyano compound is employed in at least a molar equivalent amount to the diamine. The two requirements of the process are: (1) the use of an equimolar or an excess amount of the cyano compound and (2) sparging the product with an inert gas. Each of these steps is necessary for the 2-piperazinone product to be effective as an $SO_2$ absorbent.

DETAILED DESCRIPTION OF THE INVENTION

The present invention is a process for obtaining 2-piperazinone and its substituted derivatives which are useful as $SO_2$ absorbents. It is an improvement over the processes previously known to the art. The reaction, which is conducted in aqueous solution, gives a good yield of the product which, after sparging, is useful without further costly and timeconsuming purification steps.

The 1-cyano-1-hydroxyalkanes, e.g 1-cyano-1-hydroxymethane (glycolonitrile, GN), and ethylenediamine or its alkyl- or hydroxyalkyl-substituted derivatives, e.g. aminoethylethanolamine, are reacted together in aqueous solution in equimolar amounts. It is preferred to use the cyano compound in slight excess since excess diamine in the product is undesirable when it is used as an $SO_2$ absorbent. The 2-piperazinone product should also be sparged with an inert gas, e.g. nitrogen or air, prior to use as an $SO_2$ absorbent. By inert gas is meant any gas which is inert under the conditions of use. Thus, in the preparation of these $SO_2$ absorbent products, two criteria must be observed—(1) the cyano compound must be employed in at least a molar equivalent amount and (2) the reaction product must be sparged with an inert gas.

The reaction of the cyano compound and an ethylenediamine compound is shown in the following reaction scheme:

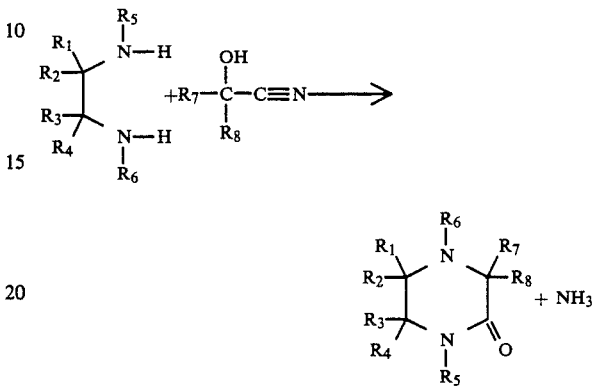

wherein $R_1$, $R_2$, $R_3$, $R_4$, $R_7$ and $R_8$ are independently hydrogen or an alkyl group having from about 1-6 carbon atoms; $R_5$ and $R_6$ are independently hydrogen, an alkyl group having from about 1-6 carbon atoms or a hydroxylalkyl group having from about 1-6 carbon atoms.

Representative compounds which are useful as sulfur dioxide absorbents and are made according to the invention are 2-piperazinone, 1,4-dimethyl-2-piperazinone, 1,4-diethyl-2-piperazinone, 1,4-di(n-butyl)-2-piperazinone, 4-methyl-2-piperazinone, 1,3,4-trimethyl-2-piperazinone, 1-(2-hydroxyethyl)-2-piperazinone [1-HEP], 4-(2-hydroxyethyl)-2-piperazinone [4-HEP], 4-(2-hydroxyethyl)-1-methyl-2-piperazinone, 4-(2-hydroxyethyl)-3-methyl-2-piperazinone, 4-(2-hydroxyethyl)-5-methyl-2-piperazinone, 1,4-bis(2-hydroxethyl)-2-piperazinone, 4-(2-hydroxyethyl)-2-piperazinone, 4-(2-hydroxypropyl)-2-piperazinone, 4-(2-hydroxybutyl)-2-piperazinone and 4-(2-hydroxypropyl)-6-methyl-2piperazinone. Other substituted piperazinones can be made by reacting the appropriately substituted ethylenediamines and 1-cyano-1hydroxyalkanes.

The following experiments show the preparation of representative substituted piperazinone products made according to the invention. The unsubstituted piperazinone is made by reacting ethylenediamine with 1-cyano-1hydroxymethane, i.e. glycolonitrile.

Preparation of 4-(2-hydroxyethyl)-2-piperazinone

A given amount of aminoethylethanolamine (AEEA) is placed in a reactor equipped with stirring means, thermometer, heating and temperature control means and means for adding the GN reactant. The AEEA is diluted with deionized water to provide a 50–75% aqueous solution. The GN may be added all at once or it may be added slowly over a period of time. If the former method is chosen, heating to the desired temperature is done post-addition. If the latter slow addition is chosen, the AEEA is heated to the desired temperature prior to the addition of the GN. After the reaction (by either method) is complete, the solution is sparged with an inert gas, e.g. nitrogen.

The cyano reactant is normally used as an aqueous solution, e.g. glycolonitrile is used as a 40 to 50% solution. While the cyano compounds could be employed in a solvent other than water, this is neither practical nor economical. The diamine reactant is also used in aqueous solution which, in the case of AEEA can be used at a concentration of from about 25 to about 75%. The dilution of the reactants is primarily for the purpose of controlling the exothermic reaction. The temperature of this reaction should be controlled within the range of from about 70° to about 100° C., preferably from about 90° to about 100° C. The reaction is conducted at atmospheric pressure. Lower or higher pressures may be employed, but to no advantage.

The preferred method of conducting the reaction is to add the cyano compound to the diamine within the optimum temperature range, the optimum pH range and over an extended period of time. Thus, the most preferred operating conditions are to add the cyano compound to the diamine at a temperature of about 100° C. at an initial pH of about 10 over a period of time of at least about one hour or more. When the addition is complete, the reaction mixture is heated for a period of time sufficient to assure that substantially all of the amine has been reacted. This can be determined by means of gas chromatography of samples taken at intervals during the course of the reaction.

The actual time of addition and subsequent heating will be determined, at least in part, by the quantity of reactants employed. At the lower temperatures, i.e. 50° to 80° C., longer addition and heating times are required.

The following examples are representative of the invention and the process was conducted either by Procedure A: combine both reactants together at room temperature and heat to the desired reaction temperature, maintaining it for the time necessary to complete the reaction; or Procedure B: heat the diamine to the desired temperature, then add the cyano compound slowly over the time required to react with the amine.

Using either procedure A or B, sufficient cyano compound is added to insure that the residual amine concentration is less than about 0.1 wt % in the final product. The process is followed by gas chromatography and the reaction is stopped when the uncharacterized intermediate peaks disappear and the concentration of the HEP reaches a maximum.

Examples 1 and 2 (shown in Table 1) were conducted according to Procedures A and B, respectively.

TABLE I

| | Reaction conditions/results | | | |
|---|---|---|---|---|
| Example No. | Temp. (°C.) | Initial pH | Molar Ratio (GN:AEEA) | Percent Yield (HEP)* |
| 1 (Procedure A) | 100 | 10.0 | 1.5:1 | 58 |
| 2 (Procedure B) | 100 | 9.8 | 1.1:1 | 87 |

*The percent yield is the total of 1-HEP and 4-HEP, both of which are good $SO_2$ absorbents In two other experiments performed according to Procedure A, the initial pH of the reaction solution (ca. 10) was adjusted by adding $H_2SO_4$ to a pH of 7.1 and of 5.2, respectively. Results showed the yields in each experiment to be substantially equivalent to the above although the ratio of 4-HEP to 1-HEP was somewhat less at the lower pH.

The slow addition of the cyano compound to the diamine, however, provides better yields of the piperazinone product. The lower yield in Example 1 is believed to be due to the hydrolysis and/or polymerization of the cyano compound. Because of the slow rate of addition in Procedure B, the cyano compound is able to react with the diamine rather than being hydrolyzed and/or polymerized.

The following experiments were performed to demonstrate the effect that residual amine (Example 3) and sparging (Example 4) have on the regenerability of the piperazinone product, i.e. the removal and recovery of the $SO_2$ from the absorbent solvent. Residual amine is present when the amine is used in molar excess instead of using equimolar quantities of reactants, or an excess of cyano compound, as required in the present invention.

EXAMPLE 3

Regenerability of $SO_2$ Absorbents (Residual Amine Effect)

Aqueous solutions of 4-(2-hydroxyethyl)-2-piperazinone were prepared containing various amounts of aminoethylethanolamine. At room temperature (23° C.), nitrogen gas containing 3% sulfur dioxide was sparged through a coarse gas dispersion tube for four hours at a rate of ca 0.5 SCFH (standard cubic feet per hour) into a known concentration of the absorbent solution. A small sample of the $SO_2$-rich absorbent solution is analyzed for $SO_3^=$ and $SO_4^=$ concentration using a standardized Ion Chromatograph. From the combined $SO_3^=$ and $SO_4^=$ concentrations the capacity of the absorbent solution for the $SO_2$ is calculated. The absorbent solution is then transferred to a flask and heated to boiling (ca. 100° C.) with a nitrogen sparge (ca 0.5 SCFH) for four hours to strip the $SO_2$ gas from the solution. During the stripping process water was added at intervals to make up for the water lost due to evaporation so that the concentration of absorbent in the solution remained constant. The solution was again analyzed for $SO_3^=$ and $SO_4^=$ concentration and the difference between the concentrations in the stripped and $SO_2$-rich solutions is used to calculate the regenerability of the absorbent solution. Table II shows the effect of residual amine on the % of $SO_2$ recovered in the regeneration step.

TABLE II

| Absorber Solution Composition | | $SO_2$ Regeneration |
|---|---|---|
| Weight % HEP | Weight % AEEA | % $SO_2$ Recovered |
| 7.6 | 20.28 | 0 |
| 5.7 | 3.28 | 0.2 |
| 5.7 | 1.28 | 5.7 |
| 5.7 | 0.28 | 64.0 |
| 10.0 | 0.009 | 95.6 |

EXAMPLE 4

Regenerability of $SO_2$ Absorbents (Effect of Sparging)

At room temperature (23° C.), nitrogen gas containing 3% sulfur dioxide was sparged into solutions of HEP, made according to Procedures A and B, through a coarse gas dispersion tube for four hours at a rate of ca 0.5 SCFH into a known concentration of the absorbent solution. A sample of the SO$_2$-rich absorbent solution is analyzed and the boiling and sparging procedure repeated as in Example 3. This solution was again analyzed for SO$_3^=$ and SO$_4^=$ concentration and the difference between the concentrations in the stripped and SO$_2$-rich solutions is used to calculate the regenerability of the absorbent solution. Table III shows the difference in regenerability of the product which had been sparged compared with one which had not been sparged. Samples 4a and 4b were prepared according to Procedures A and B, respectively. Each was sparged with N$_2$ for four hours at a rate of ca 0.5 SCFH. Sample 4c was prepared according to Procedure B, but was not sparged.

TABLE III

| Sample Number | Conditions/Results | | |
|---|---|---|---|
| | Ratio 4HEP/1HEP | Hours sparged | % Regenerability |
| 4a | 4.4/1 | 4 | 87 |
| 4b | 5.4/1 | 4 | 96 |
| 4c | 5.4/1 | 0 | 60 |

We claim:

1. In a process for making 2-piperazinones wherein a 1-cyano-1-hydroxyalkane and an ethylenediamine or a substituted ethylenediamine are contacted the improvement which comprises (1) reacting at least one mole of the cyano compound per mole of amine or substituted amine compound and (2) sparging the resulting product with an inert gas.

2. The process of claim 1 wherein the cyano compound is in molar excess.

3. The process of claim 2 wherein the molar ratio of cyano compound to amine compound is from about 1.1/1 to about 1.5/1.

4. The process of claim 2 wherein the temperature is in the range of from about 50° to about 100° C.

5. The process of claim 4 wherein the temperature is in the range of from about 80° to about 100° C.

6. The process of claim 1 wherein the reactants comprise about 25 to about 50% of the reaction mixture.

7. The process of claim 4 wherein the initial pH is from about 5 to about 10.

8. The process of claim 7 wherein the initial pH is about 10.

9. The process of claim 1 wherein the product 2-piperazinone has the formula

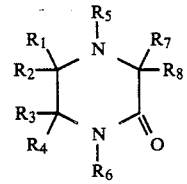

wherein R$_1$, R$_2$, R$_3$, R$_4$, R$_7$ and R$_8$ are each independently hydrogen or an alkyl group having from 1-6 carbon atoms and R$_5$ and R$_6$ are each independently hydrogen, an alkyl group having from 1-6 carbon atoms or a hydroxyalkyl group having from 1 to 6 carbon atoms.

10. The process of claim 9 wherein R$_1$, R$_2$, R$_3$, R$_4$, R$_5$, R$_6$, R$_7$ and R$_8$ are each hydrogen.

11. The process of claim 9 wherein R$_1$, R$_2$, R$_3$, R$_4$, R$_7$ and R$_8$ are each hydrogen and R$_5$ and R$_6$ are each alkyl.

12. The process of claim 11 wherein the alkyl groups are each methyl.

13. The process of claim 9 wherein R$_1$, R$_2$, R$_3$, R$_4$, R$_6$, R$_7$ and R$_8$ are each hydrogen and R$_5$ is hydroxyalkyl.

14. The process of claim 9 wherein R$_1$, R$_2$, R$_3$, R$_4$, R$_5$, R$_7$ and R$_8$ are each hydrogen and R$_6$ is hydroxyalkyl.

15. The process of claim 13 wherein the hydroxyalkyl group is hydroxyethyl.

16. The process of claim 14 wherein the hydroxyalkyl group is hydroxyethyl.

17. The process of claim 9 wherein R$_1$, R$_2$, R$_3$, R$_4$, R$_7$ and R$_8$ are each hydrogen and R$_5$ and R$_6$ are each hydroxyalkyl.

18. The process of claim 17 wherein the hydroxyalkyl groups are each hydroxyethyl.

19. The process of claim 9 wherein the product 2-piperazinone is a product mixture of a compound wherein R$_1$, R$_2$, R$_3$, R$_4$, R$_5$, R$_7$ and R$_8$ are each hydrogen and R$_6$ is hydroxyalkyl and a compound wherein R$_1$, R$_2$, R$_3$, R$_4$, R$_6$, R$_7$ and R$_8$ are each hydrogen and R$_5$ is hydroxyalkyl.

20. The process of claim 19 wherein the hydroxyalkyl group in each compound is hydroxyethyl.

21. The process of claim 1 wherein the reaction product is sparged with nitrogen.

22. The process of claim 1 wherein the reaction is conducted in aqueous medium.

* * * * *